United States Patent [19]

Honda et al.

[11] Patent Number: 5,468,474
[45] Date of Patent: Nov. 21, 1995

[54] N-ACYLGLUTAMINE DERIVATIVES AND COSMETIC COMPOSITIONS

[75] Inventors: Shinkichi Honda, Abiko; Kenji Torii, Inashiki; Yoichiro Arai, Kodama; Masaji Kasai, Fujisawa; Hiromasa Kato, Sunto; Takao Iida, Tama; Tomoya Takahashi, Tsuchiura; Yoshiharu Yokoo, Ushiku; Toshikazu Kamiya; Tatsuya Tamaoki, both of Machida, all of Japan

[73] Assignee: Kyowa Hakko Kogyo Co., Ltd., Tokyo, Japan

[21] Appl. No.: 256,942

[22] PCT Filed: Dec. 9, 1993

[86] PCT No.: PCT/JP93/01785

§ 371 Date: Jul. 27, 1994

§ 102(e) Date: Jul. 27, 1994

[87] PCT Pub. No.: WO94/13624

PCT Pub. Date: Jun. 23, 1994

[30] Foreign Application Priority Data

Dec. 9, 1992 [JP] Japan .................. 4-329663

[51] Int. Cl.$^6$ .................. A61K 7/06; C07D 311/20; C07C 69/00
[52] U.S. Cl. .................. 424/70.1; 424/59; 424/401; 514/844; 514/847; 549/406; 552/544; 560/142; 560/145
[58] Field of Search .................. 560/142, 145; 424/401, 70, 59, 70.1; 514/844, 847; 552/544; 549/406

[56] References Cited

U.S. PATENT DOCUMENTS

| | | | |
|---|---|---|---|
| 3,969,087 | 7/1976 | Saito et al. | 44/7 |
| 3,979,449 | 9/1976 | Hirsbrunner et al. | 260/534 E |
| 4,760,095 | 7/1988 | Djerassi et al. | 514/847 |
| 5,112,613 | 5/1992 | Honda et al. | 424/400 |
| 5,153,340 | 10/1992 | Ichikawa et al. | 552/509 |

FOREIGN PATENT DOCUMENTS

| | | |
|---|---|---|
| 0231777 | 8/1987 | European Pat. Off. |
| 0443592 | 8/1991 | European Pat. Off. |
| 7940 | 1/1977 | Japan . |
| 20438 | 2/1978 | Japan . |
| 223206 | 10/1991 | Japan . |
| 1522212 | 8/1978 | United Kingdom . |

Primary Examiner—Jyothsna Venkat
Attorney, Agent, or Firm—Fitzpatrick, Cella, Harper & Scinto

[57] ABSTRACT

The present invention relates to N-acylglutamine derivatives of formula (I):

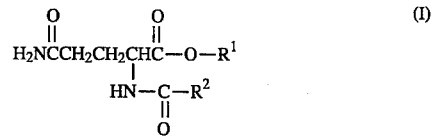

The N-acylglutamine derivatives are well compatible with oily bases and have good skin-moisturizing activity and hair growth-stimulative effect. These are useful as cosmetics and hair growth stimulants.

8 Claims, No Drawings

N-ACYLGLUTAMINE DERIVATIVES AND COSMETIC COMPOSITIONS

TECHNICAL FIELD

The present invention relates to N-acylglutamine derivatives and to cosmetics and hair growth stimulants containing the N-acylglutamine derivatives.

PRIOR ART

Japanese Published Unexamined Patent Application No. 20438/78 discloses cosmetics containing esters of N-acylamino acids, and Japanese Published Unexamined Patent Application No. 223206/91 (corresponding to U.S. Pat. No. 5,112,613) discloses cosmetics containing N-acylglutamine (NAG).

NAG is stable but is poorly compatible with oily bases, and emulsion in cosmetics is often unstable to lower the viscosity of cosmetics containing NAG. Therefore, kinds of cosmetics containing NAG and the amounts of NAG contained in cosmetics are limited.

The object of the present invention is to provide N-acylglutamine derivatives which are more compatible with oily bases than NAG and are therefore stable in cosmetics and hair growth stimulants to have good skin-moisturizing activity in cosmetics and hair growth-stimulative effect in hair growth stimulants.

DISCLOSURE OF THE INVENTION

The present invention relates to N-acylglutamine derivatives represented by formula (I):

$$\underset{\underset{\underset{O}{\|}}{\underset{HN-C-R^2}{|}}}{H_2NCCH_2CH_2CHC-O-R^1} \quad (I)$$

wherein $R^1$ represents an alkyl having 12 to 22 carbon atoms, an alkenyl having 12 to 22 carbon atoms,

[chroman/tocopherol structure with CH₃ groups and CH₂—[(CH₂)₂CH(CH₃)CH₂]₃H],

[cholesterol-type steroid structure with CH₃ groups],

[phenol: —⟨benzene⟩—OH], or

[—⟨benzene⟩—O—CCHCH₂CH₂CNH₂ with HNCR³ group]

wherein $R^3$ represents an alkyl having 1 to 6 carbon atoms; and
$R^2$ represents an alkyl having 1 to 6 carbon atoms.

The present invention also relates to cosmetics and hair growth stimulants containing the N-acylglutamine derivatives.

The alkyl having 1 to 6 carbon atoms for the definitions of $R^2$ and $R^3$ is a linear or branched alkyl including methyl, ethyl, propyl, isopropyl, butyl, t-butyl, pentyl and hexyl groups. The alkyl having 12 to 22 carbon atoms for the definition of $R^1$ is a linear or branched alkyl group including dodecyl, tridecyl, tetradecyl, pentadecyl, hexadecyl, heptadecyl, stearyl, isostearyl, myristyl, octadecyl, nonadecyl, eicosanyl, henicosanyl and docosanyl groups. The alkenyl having 12 to 22 carbon atoms is a linear or branched alkenyl group including oleyl, dodecenyl, elaidyl, linoleyl and linolenyl groups.

Compounds represented by formulae (I), (II), (III), . . . are hereinafter referred to as Compound (I), Compound (II), Compound (III), . . . , respectively.

Methods for producing Compounds (I) are mentioned below.

Method 1:

$$H_2NCCH_2CH_2CHC-O-H + R^1OH \longrightarrow$$
$$\text{(II)} \quad \text{(III)}$$

$$H_2NCCH_2CH_2CHC-O-R^1 \xrightarrow[\text{ii) Acid Anhydride or Acid Halide}]{\text{i) Removal of Protective Group}}$$
$$\text{(IV)}$$

$$H_2NCCH_2CH_2CHC-O-R^1$$
$$\underset{\underset{O}{\|}}{HN-C-R^2}$$
$$\text{(I)}$$

wherein $R^1$ and $R^2$ have the same meanings as defined above; and P represents a protective group for the amino group.

As the protective group for the amino group, t-butoxycarbonyl group, benzyloxycarbonyl group, etc. are used.

Compound (IV) may be obtained by reacting Compound (II) with 0.8 to 2 equivalents of Compound (III) in a solvent in the presence of a condensing agent such as dicyclohexylcarbodiimide, at a temperature from −80° C. to 40° C. for 30 minutes to 2 days.

As the reaction solvent, tetrahydrofuran (THF), dioxane, dimethylformamide (DMF), dimethylsulfoxide (DMSO), etc. are used.

Compound (I) may be obtained by removing the amino-protective group of Compound (IV) in a solvent by trifluoroacetic acid (TFA), catalytic reduction, etc., followed by acylating it with an acid anhydride such as acetic anhydride, or with an acid halide such as acetyl chloride at 0° to 80° C for 30 minutes to 2 days. The abovementioned solvents may be used as the reaction solvent.

Compound (II), the starting material, may be obtained by introducing the above-mentioned protective group into a commercially available L-glutamine by a conventional method, or a commercial product of Compound (II) may be used.

Method 2:

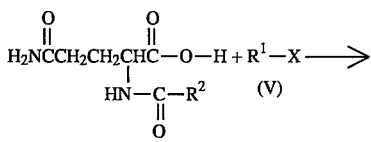

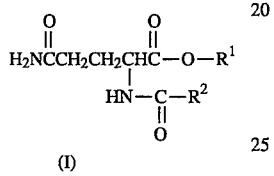

(I)

wherein $R^1$ and $R^2$ have the same meanings as defined above; and X represents a halogen atom.

The halogen atom includes chlorine atom, iodine atom and bromine atom.

Compound (I) may be obtained by reacting an N-acyl-glutamine with 0.8 to 2 equivalents of Compound (V) in the presence of a base such as sodium hydride, cesium fluoride, triethanolamine and cesium carbonate, if necessary.

As the reaction solvent, DMF, THF, DMSO, dioxane, etc. are used. The reaction is carried out at 0° to 100° C. and is finished in 10 minutes to one day.

The products obtained in the above-mentioned steps may be isolated and purified by conventional purification methods which are generally used in the field of organic synthetic chemistry, for example, by filtration, extraction, washing, drying, concentration, recrystallization, various chromatographic methods.

Specific examples of Compound (I) are shown in Table 1.

TABLE 1

| Compound | Structural Formula |
| --- | --- |
| Compound 1 | ![Compound 1 structure: tocopherol derivative with H2NCCH2CH2CHC-O- linked to a chromanol ring bearing CH3 groups and a CH2+(CH2)2CH(CH3)CH2]3H side chain; HN—CCH3 substituent] |
| Compound 2 | H2NCCH2CH2CHC—O—CH2CH with CH(CH3)CH2C(CH3)3 and CH2CH2CH(CH3)CH2C(CH3)3 branches; HN—CCH3 |
| Compound 3 | H2NCCH2CH2CHC—O— linked to cholesterol skeleton; HN—CCH3 |
| Compound 4 | H2NCCH2CH2CHC—O—(CH2)17CH3; HN—CCH3 |

TABLE 1-continued

| Compound | Structural Formula |
|---|---|
| Compound 5 | $\text{H}_2\text{NCCH}_2\text{CH}_2\text{CH}-\overset{\text{O}}{\overset{\|}{\text{C}}}-\text{O}-\text{C}_6\text{H}_4-\text{OH}$ with $\text{HN}-\overset{\text{O}}{\overset{\|}{\text{CCH}_3}}$ and terminal $\overset{\text{O}}{\overset{\|}{\text{C}}}$ |
| Compound 6 | $\text{H}_2\text{NCCH}_2\text{CH}_2\text{CH}-\overset{\text{O}}{\overset{\|}{\text{C}}}-\text{O}-\text{C}_6\text{H}_4-\text{O}-\overset{\text{O}}{\overset{\|}{\text{C}}}-\text{CH}-\text{CH}_2\text{CH}_2\text{CNH}_2$ with $\text{HN}-\overset{\text{O}}{\overset{\|}{\text{CCH}_3}}$ groups |

Compound (I) has an excellent skin-moisturizing activity and is used in cosmetics of various forms, for example, skin-care products such as lotion, emulsion, cream, soap and pack; make-up products such as lipstick, foundation, eye shadow, eye liner; and hair-care products such as shampoo and rinse.

Cosmetics of the present invention may be produced by blending by a conventional method Compound (I) and various components which are generally used for producing cosmetics, such as fats and oils, hydrocarbons, waxes, fatty acids, synthetic esters, alcohols, surfactants, thickeners, moisturizers, preservatives, fragrances, pigments, pharmaceutical chemicals and purified water, by a conventional methods.

In order to improve the spreadability of the cosmetics on the skin, the adhesiveness thereof to the skin and the water-repelling property thereof on the skin, it is recommended to use pigments coated with Compound (I).

The content of Compound (I) in cosmetics may be from 0.001 to 10.0 w/w %, preferably from 0.005 to 5.0 w/w %, of the total weight of the cosmetics. ("%" is herein w/w %.)

Examples of fats and oils include jojoba oil, castor oil, olive oil, soybean oil, coconut oil, palm oil, cacao butter, mink oil, turtle oil and coconut oil fatty acid diethanolamides.

Examples of hydrocarbons include liquid paraffin, vaseline, microcrystalline wax and squalane.

Examples of waxes include beeswax, lanolin, carnauba wax and candelilla wax.

Examples of fatty acids include myristic acid, palmitic acid, stearic acid, oleic acid and isostearic acid.

Examples of synthetic esters include isopropyl myristate, isopropyl palmitate, butyl oleate, myristyl myristate, octyldecyl myristate, propylene glycol monostearate, myristyllactate, isostearyl malate, glycerine monostearate and distearyldimethyl ammonium chloride.

Fats and oils, hydrocarbons, waxes, fatty acids and synthetic esters are contained in the cosmetics in an amount of 0 to 30%.

Examples of alcohols include ethanol, 1,3-butylene glycol, propylene glycol, lauryl alcohol, cetanol, stearyl alcohol, oleyl alcohol. Alcohols are contained in the cosmetics in an amount of 0 to 25%.

Examples of surfactants include polyoxyethylene-hardened castor oil, sodium lauryl sulfate, polyoxyethyleneglyceryl pyroglutamate isostearate, sodium alkylbenzene sulfonates, polyoxyethylene(10) stearyl ether, dialkyl sulfosuccinates, cetylpyridinium bromide, n-octadecyl trimethylammonium chloride, monoalkyl phosphates, N-acylglutamic acids, sucrose fatty acid esters, polyoxyethylene(20) sorbitan monostearate, sodium polyoxyethylene lauryl ether sulfate and polyoxyethylene-reduced lanolin.

The surfactants are usually employed in the cosmetics in an amount of 0.1 to 5% and in the case of a shampoo, in an amount of 0.1 to 40%.

Examples of thickeners include carboxyvinyl polymers, methylpolysiloxanes, dextran, carboxymethyl cellulose, carrageenan, hydroxypropylmethyl cellulose. Thickeners are contained in the cosmetics in an amount of 0 to 0.5%.

Examples of moisturizers include glycerin, propylene glycol, 1,3-butylene glycol, pyrrolidonecarboxylic acid, lactic acid and hyaluronic acid. Moisturizers are contained in the cosmetics in an amount of 0 to 25%.

Examples of antiseptics include benzoic acid, salicylic acid, dehydroacetic acid, their salts, phenols such as parahydroxybenzoates, triclosan, halocarban. Preservatives are contained in the cosmetics in an amount of 0 to 0.3%.

Any fragrances which are conventionally used in cosmetics may be used.

Examples of pigments include iron oxide, titanium dioxide, zinc oxide, kaolin and talc. Pigments are contained in the cosmetics in an amount of 0 to 1%. Pigments coated with Compound (I) maybe produced by uniformly dispersing pigments and Compound (I) dissolved in an alcohol such as ethyl alcohol, removing the solvent by distillation to obtain dry coated pigments and grinding them.

Examples of pharmaceutical chemicals include wheat germ oil, vitamin E, vitamin A, vitamin $B_2$, magnesium L-ascorbyl 2-phosphate, D-pantothenyl alcohol, dipotassium glycyrrhetinate and glutathione. Pharmaceutical chemicals are contained in the cosmetics in an amount of 0 to 5%.

Since Compound (I) have an excellent hair growth-stimulative effect as shown in Test Examples mentioned hereinafter, it may be used as hair growth stimulating tonic, hair growth stimulating lotion, hair growth stimulating cream, etc.

The hair growth stimulants of the present invention may be produced by blending Compound (I) and various components which are conventionally used in producing hair growth stimulants, such as alcohols, fats and oils, fragrances, surfactants, microbicides, antioxidants, vitamins, antiinflammatory agents, refreshing agents, herb extracts and purified water by a conventional methods.

The content of Compound (I) in hair growth stimulants may be from 0.01 to 30%, preferably from 0.1 to 10%, of the total weight of the hair growth stimulants.

Examples of alcohols include ethanol, glycerin, 1,3-butylene glycol and propylene glycol.

Examples of fats and oils include wheat germ oil, camellia oil, jojoba oil, olive oil, squalane, safflower oil, macadamia nut oil, avocado oil and soybean hydrogenated lecithin.

Any fragrances which are conventionally used in hair growth stimulants may be used.

Examples of surfactants include polyoxyethylene(60) hardened castor oil, polyoxyethylene(8) oleyl ether, polyoxyethylene(10) monooleate, polyoxyethylene(30) glyceryl monostearate, sorbitan monostearate, polyoxyethylene(20) sorbitan monooleate, sucrose fatty acid esters, hexaglyceryl monolaurate and polyoxyethylene-reduced lanolin.

Examples of microbicides include hinokitiol, triclosan, chlorohexidylgluconic acid salts, phenoxyethanol, resorcinol, isopropylmethylphenol, azulene, salicylic acid, light-sensitive elements and zinc pyrithione.

Examples of antioxidants include butylhydroxyanisole, butylhydroxytoluene, gallic acid, propyl gallate and erysorbic acid.

Examples of vitamins include dl-α-tocopherol acetate, dl-α-tocopherol, vitamin E, benzyl nicotinate, D-pantothenyl alcohol, pantothenyl ethyl ether, biotin, pyridoxine hydrochloride and riboflavin.

Examples of anti-inflammatory agents include dipotassium glycyrrhetinate and allantoin.

Examples of refreshing agents include capcicum tincture and 1-menthol.

Examples of herb extracts include Swertia Japonica Makino extract, garlic extract, ginseng extract and aloe extract.

Solubilities of Compounds (I) and NAG in various oily bases are shown below.

0.2 g of one of Compound (I) (Compounds 1 to 4) or NAG and 19.8 g of the oily base shown in Table 2 were put in a beaker and stirred under heating. The temperature at which Compound (I) or NAG was completely dissolved in the oily base was measured. The results are shown in Table 2.

TABLE 2

| Oily Base | Compound | | | | |
|---|---|---|---|---|---|
| | Compound 1 | Compound 2 | Compound 3 | Compound 4 | NAG |
| Liquid Paraffin | 125 | 85 | >175 | 115 | Insoluble |
| Squalane | 130 | 110 | >180 | 120 | Insoluble |
| Jojoba oil | >150 | 80 | 160 | 105 | Insoluble |
| Isopropyl Myristate | 130 | 40 | 160 | 105 | Insoluble |
| Castor Oil | 110 | 40 | 160 | 105 | Insoluble |
| Propylene Glycol | 90 | RT | 105 | 85 | Insoluble |
| Ethanol | 40 | RT | 60 | 40 | Insoluble |

RT: Room Temperature (°C.)

As is apparent from Table 2, Compound (I) is more soluble in various oily bases than NAG.

Next, sensory tests (moistness of skin, etc.) of cosmetics containing Compound. (I) and hair growth-stimulative effect of Compound (I) will be explained below.

TEST EXAMPLE 1:

Sensory Test of Lotion

The lotions obtained in Example 7 and Comparative Example 1 were separately applied to the face of 25 professional panelists, twice (in the morning and the evening) a day, continuously for one month.

The results are shown in Table 3.

TABLE 3

| | Lotion | | | | | |
|---|---|---|---|---|---|---|
| | Example 7 | | | Comparative Example 1 | | |
| Total Evaluation | ⊚ | ○ | Δ | ⊚ | ○ | Δ |
| (a) Smoothness of skin | 22 | 2 | 1 | 2 | 9 | 14 |
| (b) Moistness of skin | 14 | 8 | 3 | 15 | 7 | 3 |
| (c) Recovery of roughening skin | 20 | 2 | 3 | 2 | 10 | 13 |

⊚: Very good. ○: Good. Δ: ordinary.

As is apparent from Table 3, the lotion of Example 7 (containing Compound 4) was much better than the lotion of Comparative Example 1 (containing NAG) with respect to the smoothness of skin and the recovery of roughening skin. With respect to the moistness of skin, the lotion of Example was comparable to the lotion of Comparative Example 1.

TEST EXAMPLE 2:

Sensory Test of Milky Lotion

The same sensory test as in Test Example 1 was carried out except that milky lotions obtained in Example 8 and Comparative Example 2 were used in place of the lotions.

The results are shown in Table 4.

TABLE 4

| | Milky Lotion | | | | | |
|---|---|---|---|---|---|---|
| | Example 8 | | | Comparative Example 2 | | |
| Total Evaluation | ⊚ | ○ | Δ | ⊚ | ○ | Δ |
| (a) Smoothness of skin | 22 | 2 | 1 | 2 | 7 | 16 |
| (b) Moistness of skin | 15 | 8 | 2 | 4 | 4 | 17 |
| (c) Softness of skin | 14 | 8 | 3 | 2 | 6 | 17 |
| (d) Recovery of roughening skin | 20 | 2 | 3 | 2 | 5 | 18 |

TEST EXAMPLE 3:

Sensory Test of Sunscreen Milky Lotion

The same sensory test as in Test Example 1 was carried out except that the sunscreen milky lotions obtained in Examples 11 and 12 were used in place of the lotions.

The results are shown in Table 5.

TABLE 5

| | Sunscreen Milky Lotion | | | | | |
|---|---|---|---|---|---|---|
| | Example 12 | | | Example 11 | | |
| Total Evaluation | ⊚ | ○ | Δ | ⊚ | ○ | Δ |
| (a) Spread on skin | 13 | 10 | 2 | 8 | 12 | 5 |
| (b) Adhesion to skin | 20 | 4 | 1 | 5 | 12 | 8 |
| (c) Water-repellent ability | 12 | 10 | 3 | 8 | 11 | 6 |

TEST EXAMPLE 4:

Hair Growth-Stimulative Effect

Hair on the back of male C3H/HeSlc-strain mice aged 9 weeks, which was in the telogen of hair cycle, was clipped off by an electric hair-clipper. As the test compound, N-acetylglutamine-isostearyl (Compound 2) obtained in Example 2 was used. The test compound was dissolved in a mixed solvent (ethanol:glycerine:1,3-butylene glycol:purified water=6:0.5:0.5:3, v/v) to prepare a 0.5% test solution. The test solution was uniformly applied to the hair removed area of each mouse of the test group once a day in an amount of 150 μl. The mixed solvent was also applied to each mouse of the control group. Hair growth-stimulative effect was estimated by scoring the hair growing area of the test compound treated group or of the control group and by measuring the mean value of the scored data in each group.

Regarding the mice of the test compound treated-group, the skin became black, indicating the formation of hair roots therein on the 10th day, and thereafter hair grew rapidly on the skin. On the 17th day, the hair growth-stimulative effect of the test compound was noticeable in the mice of the test compound treated group. On the other hand, the hair growing area of the mice of the control group was very small even on 17th day.

The results are shown in Table 6.

On about the 20th day, hairs grew almost completely in the hair removed area of the mice of the test compound treated group, and anything wrong such as inflammation was not found in the test compound applied area.

TABLE 6

| Test Solution | Sum of Scores* |
|---|---|
| Control Group | 6 |
| Test Group | 12 |

*: Sum of scores of five mice in each group.
Score:
0: No hairs grew.
1: A few hairs grew.
2: Some hairs grew to a middle degree.
3: Hairs grew all over the clipped area.

BEST MODE FOR CARRYING OUT THE INVENTION

Examples and Comparative Examples are mentioned hereunder.

EXAMPLE 1:

N-acetylglutamine-tocopheryl (Compound 1)

In 1200 ml of dried THF were dissolved 30 g (107 mmol) of N-benzyloxycarbonyl-L-glutamine (hereinafter referred to as Z-L-glutamine), 46 g (107 mmol) of tocopherol and 1 g of 4-dimethylaminopyridine, and cooled to 0° C. Then, 44.1 g (214 mmol) of dicyclohexylcarbodiimide (DCC) was added thereto and allowed to stand at 0° C. for 3 hours. The reaction mixture was allowed to stand in a cold room at 3° C. for further 15 hours. Dicyclohexylurea (DCU) precipitated was removed, and the reaction mixture was again allowed to be cooled at 3° C. DCU precipitated was removed, and the reaction mixture was concentrated under reduced pressure to obtain a gel-like substance, and then 500 ml of hexane were added to the obtained gel-like substance. The mixture was triturated and then subjected to centrifugation to remove hexane therefrom. The obtained precipitate was washed three times with hexane and then dried under reduced pressure to obtain a residue. The residue was dissolved in 500 ml of chloroform and then subjected to silica gel column chromatography (chloroform:acetone=4:1, v/v). The main fraction of the eluate was concentrated and again subjected to silica gel column chromatography (chloroform:methanol= 9:1, v/v). The main fraction of the eluate was concentrated under reduced pressure to obtain 40.8 g of a white powder. The obtained white powder was dissolved in a mixed solvent of 700 ml of THF and 480 ml of acetic anhydride, and 10 g of 10% Pd-C (50% $H_2O$) were added thereto, and aerated with hydrogen gas for 7 hours. The solution was filtered, and the filtrate was dried under reduced pressure to obtain a residue. The residue was dissolved in chloroform and. subjected to silica gel column chromatography (chloroform:methanol=9:1, v/v). The main fraction of the eluate was concentrated under reduced pressure to obtain 28 g of Compound 1 as a white powder.

Appearance: colorless powder
Melting Point: 144.0°–145.2 °C.
Specific Rotatory Power: $[\alpha]_D^{23}$=–30.9° (C 1.16, $CH_3OH$)
Ultraviolet Absorption Spectrum ($CH_3OH$ solution): λ max nm (ε) 225.0 (shoulder, 11,000), 277.1 (1,900), 283.5 (2,000)
Infrared Absorption Spectrum (KBr tablet): ν max $cm^{-1}$ 3415, 3332, 3210, 2925, 2868, 1741, 1666, 1641, 1545, 1462, 1209, 1167
FAB-MS Spectrum (matrix: m-nitrobenzyl alcohol): m/z 601 (M+I)
HR-FAB-MS: $C_{36}H_{61}N_2O_5$ Measured: 601.4590 Calculated: 601.4581
$^1H$ NMR Spectrum (400 MHz, $CDCl_3$ solution): δ ppm (integral, multiplicity) 0.84 (3H, d), 0.85 (3H, d), 0.87 (6H, d), 1.00–1.62 (22H, m), 1.65–1.90 (4H, m), 1.96 (3H, s), 1.99 (3H, m), 2.05 (3H, m), 2.08 (3H, m), 2.10–2.30 (1H, m), 2.30–2.54 (3H, m), 2.57 (2H, t), 4.87 (1H, m), 5.58 (1H, brs), 6.19 (1H, brs), 6.78 (1H, brs)
$^{13}C$ NMR Spectrum (100 MHz, $CDCl_3$ solution): δ ppm 11.82, 12.14, 12.99, 19.60, 19.63, 19.66, 19.70, 19.76, 20.16, 21.05, 22.63, 22.72, 23.09, 24.45, 24.81, 27.99, 28.16, 31.04, 32.07, 32.71, 32.79, 37.31, 37.37, 37.41, 37.48, 37.58, 39.43, 52.27, 75.20, 117.59, 123.24, 124.81, 126.44, 140.16, 149.71, 170.80, 170.83, 174.60
Elementary Analysis: $C_{36}H_{60}N_2O_5$ Measured: C 71.68 H 10.33 N 4.43 Calculated: C 71.96 H 10.07 N 4.66

EXAMPLE 2:

N-acetylglutamine-isostearyl (Compound 2)

In 700 ml of dried THF were dissolved 20 g (71.36 mmol) of Z-L-glutamine, 17.7 g (65.4 mmol) of isostearyl alcohol and 580 mg of 4-dimethylaminopyridine and cooled to 0° C. Then, 14.7 g (71.24 mmol) of DCC was added thereto and allowed to stand at 0° C. for 3 hours. The reaction mixture was allowed to stand in a cold room at 3° C. for further 15 hours. DCU precipitated was removed, and the reaction mixture was again allowed to be cooled at 3° C. DCU precipitated was removed, and the reaction mixture was concentrated under reduced pressure and subjected to silica gel column chromatography (hexane:methanol=8:2, v/v). The main fraction of the eluate was concentrated to obtain 22.5 g of a caramel-like substance.

The substance was dissolved in a mixed solvent of 300 ml of THF and 40 ml of acetic anhydride. 3.5 g of 10% Pd-C (50% $H_2O$) was added thereto, and aerated with hydrogen gas for 7 hours. The solution was filtered, and the filtrate was concentrated under reduced pressure. The residue was subjected to silica gel column chromatography (ethyl acetate: ethanol=8:2, v/v). The main fraction of the eluate was concentrated under reduced pressure to obtain a caramel-like substance.

The caramel-like substance was dissolved in 100 ml of ethyl acetate, washed three times with 50 ml of 1% sodium bicarbonate and then once with 100 ml of water, dehydrated with magnesium sulfate and then concentrated under reduced pressure. The residue was subjected to silica gel column chromatography (ethyl acetate: ethanol=8:2, v/v). The main fraction was concentrated to obtain 13.5 g of Compound 2 as white crystals.
Appearance: colorless powder
Melting Point: 67.0°–68.0° C.
Specific Rotatory Power: $[\alpha]_D^{23} = -18.2°$ (C 1.33, $CH_3OH$)
Ultraviolet Absorption Spectrum ($CH_3OH$ solution): $\lambda$ max nm ($\epsilon$) terminal absorption only
Infrared Absorption Spectrum (KBr tablet): $\nu$ max $cm^{-1}$ 3415, 3288, 2954, 1743, 1655, 1552, 1636, 1302, 1244, 1176
FAB-MS Spectrum (matrix: m-nitrobenzyl alcohol): m/z 441 (M+1)
HR-FAB-MS: $C_{25}H_{49}N_2O_4$ Measured: 441.3 685 Calculated: 441.3692
$^1$H NMR Spectrum (400 MHz, $CDCl_3$ solution): $\delta$ ppm (integral, multiplicity) 0.70–1.00(24H, m), 1.00–1.60(10H, m), 1.60–1.80(10H, m), 1.85–2.05 (1H, m), 2.03 (3H, s), 2.10–2.40 (3H, m), 4.07(2H, m), 4.62(1H, m), 5.61(1H, brs), 6.19(1H, brs), 6.57 (1H, m)
$^3$C NMR Spectrum (100 MHz, $CDCl_3$ solution): $\delta$ ppm 18.40, 18.47, 18.54, 18.62, 18.69, 22.53, 22.64, 22.71, 23.15, 24.93, 25.01, 26.43, 26.52, 28.43, 29.32, 29.42, 29.53, 29.60, 29.63, 29.72, 29.88, 29.91, 29.95, 30.04, 30.08, 30.10, 31.07, 31.20, 31.93, 37.60, 37.63, 37.72, 37.75, 37.91, 37.99, 44.53, 44.59, 44.62, 48.26, 48.34, 48.44, 48.48, 48.61, 48.66, 51.17, 51.30, 51.40, 52.09, 67.08, 67.13, 67.16, 67.38, 67.42, 170.49, 172.12, 172.16, 174.49
Elementary Analysis: $C_{25}H_{48}N_2O_4$ Measured: C 67.79 H 11.23 N 6.15 Calculated: C 68.14 H 10.98 N 6.36

EXAMPLE 3:

N-acetylglutamine-cholesteryl (Compound 3)

In 600 ml of dried THF were dissolved 14.06 g (50.17 mmol) of Z-L-glutamine, 19.4 g (50.17 mmol) of cholesterol and 380 mg of 4-dimethylaminopyridine and cooled to 0° C. Then, 10.22 g (49.5 mmol) of DCC was added thereto and allowed to stand at 0° C. for 3 hours. The reaction mixture was then allowed to stand in a cold room at 3° C. for further 15 hours. DCU precipitated was removed, and the reaction mixture was again allowed to be cooled at 3° C. DCU precipitated was removed, and the reaction mixture was concentrated under reduced pressure. The residue was subjected to silica gel column chromatography (hexane:ethyl acetate=7:3, v/v). The main fraction of the eluate was concentrated to obtain 20.3 g of a white powder. This operation was repeated three times and 44.9 g of the substance obtained was dissolved in a mixed solvent of 1000 ml of THF and 32.6 ml of acetic anhydride. 6 g of 10% Pd-C (50% $H_2O$) was added thereto, and aerated with hydrogen gas for 6 hours. The solution was filtered, and the filtrate was concentrated under reduced pressure. The residue was subjected to silica gel column chromatography (chloroform:ethanol=8:2, v/v). The main fraction of the eluate was concentrated under reduced pressure to obtain 20.7 g of Compound 3 as a white powder.
Appearance: colorless powder
Melting Point: 182.0°–184.0° C.
Specific Rotatory Power: $[\alpha]_D^{23} = -32.5°$ (c 0.44, $CH_3OH$)
Ultraviolet Absorption Spectrum ($CH_3OH$ solution): $\lambda$ max nm ($\epsilon$) terminal absorption only
Infrared Absorption Spectrum (KBr tablet): $\nu$ max $cm^{-1}$ 3423, 3298, 2935, 1739, 1664, 1541, 1375, 1207, 1136, 1007
FAB-MS Spectrum (matrix: m-nitrobenzyl alcohol): m/z 557 (M+H)
HR-FAB-MS: $C_{34}H_{57}N_2O_4$ Measured: 557.4136 Calculated: 557.4319
$^1$H NMR Spectrum (400 MHz, $CDCl_3$ solution): $\delta$ ppm (integral, multiplicity) 0.68 (3H, s), 0.86 (3H, d), 0.87 (3H, d), 0.92 (3H, d), 1.02 (3H, s), 0.85–1.02 (3H, m), 1.02–1.70 (17H, m), 1.78–2.03(7H, m), 2.03(3H, s), 2.15–2.23(1H, m), 2.26–2.40 (4H, m), 4.55 (1H, m), 4.67 (1H, m), 5.37 (1H, brd), 5.58(1H, brs), 6.36(1H, brs), 6.58(1H, d)
$^{13}$C NMR Spectrum (100 MHz, $CDCl_3$ solution): $\delta$ ppm 11.87, 18.74, 19.30, 21.05, 22.57, 22.82, 23.18, 23.86, 24.30, 27.68, 28.02, 28.24, 28.80, 31.36, 31.93, 32.00, 35.80, 36.22, 36.92, 37.95, 39.54, 39.75, 42.35, 50.05, 52.07, 56.20, 56.73, 75.70, 123.07, 139.24, 170.66, 171.47, 174.63
Elementary Analysis: $C_{34}H_{56}N_2O_4$ Measured: C 72.96 H 10.46 N 4.99 Calculated: C 73.34 H 10.14 N 5.03

EXAMPLE 4:

N-acetylglutamine-stearyl (Compound 4)

In 186 ml of DMF was dissolved 9.3 g (0.0495 tool) of N-acetyl-L-glutamine, 2.18 g (0.0545 mol) of 60% sodium hydride was added thereto, and stirred for 30 minutes at 10° C. Then, 20.7 g (0.0545 tool) of stearyl iodide was added thereto and reacted at 60° C. for 5 hours. After the reaction was completed, the reaction mixture was poured into 2 liter of water. The crystals precipitated were dissolved in 1 liter of ethyl acetate under heating, dried with magnesium sulfate and then concentrated under reduced pressure. The residue was cooled, and the crystals precipitated were taken out by filtration. The obtained crystals were subjected to silica gel column chromatography (chloroform:methanol= 10:1, v/v) to obtain 13 g of Compound 4 as white crystals.
Appearance: colorless powder
Melting Point: 118.0°119.0° C.
Specific Rotatory Power: $[\alpha]_D^{23}=+6.7°$ (C 1.06, $CHCl_3$)
Ultraviolet Absorption Spectrum ($CH_3OH$ solution): $\lambda$ max nm ($\epsilon$) terminal absorption only
Infrared Absorption Spectrum (KBr tablet): $\nu$ max $cm^{-1}$ 3419, 3332, 3209, 2916, 2848, 1732, 1664, 1635, 1549, 1471, 1415, 1311, 1223, 1176, 719
FAB-MS Spectrum (matrix: m-nitrobenzyl alcohol): m/z 441 (M+H)
HR-FAB-MS: $C_{25}H_{49}N_2O_4$ Measured: 441.3710 Calculated: 441.3692 p0 $^1$H NMR Spectrum (400 MHz, $CDCl_3$ solution): $\delta$ ppm (integral, multiplicity) 0.88 (3H, d), 1.20–1.70 (32H, m), 1.80–2.00 (1H, m), 2.04(3H, s), 2.05–2.40(3H, m), 4.14(2H, t), 4.59(1H, m), 5.37(1H, brs), 6.21(1H, brs), 6.45(1H, d)
$^{13}$C NMR Spectrum (100 MHz, $CDCl_3$ solution): $\delta$ ppm 14.15, 22.73, 23.24, 25.84, 28.55, 28.77, 29.24, 29.40, 29.53, 29.63, 29.70, 29.74, 31.97, 32.00, 52.03, 66.05, 170.62, 172.08, 174.43

Elementary Analysis: $C_{25}H_{48}N_2O_4$ Measured: C 67.87 H 11.29 N 6.16 Calculated: C 68.14 H 10.98 N 6.36

EXAMPLE 5:
O-(N-acetyl-L-glutaminyl)hydroquinone
(Compound 5)

In 700 ml of THF were dissolved 14 g (49.95 mmol) of N-Z-L-glutamine, 10 g (49.94 mmol) of monobenzylhydroquinone and 0.4 g of 4-dimethylaminopyridine and cooled to 0° C. Then, 10.3 g (49.92 mmol) of DCC was added thereto and stirred at 0° C. for 20 hours. DCU precipitated was removed by filtration, and the filtrate was concentrated under reduced pressure. The residue was dissolved in 1.2 liter of THF, 3.66 ml (38.8 mmol) of acetic anhydride and 3.5 g of 10 % Pd-C catalyst (50% $H_2O$) were added thereto, and aerated with hydrogen gas for 5 hours. The catalyst was removed by filtration, and the filtrate was concentrated under reduced pressure. The residue was subjected to silica gel column chromatography (chloroform:methanol=9: 1, v/v), and the main fraction of the eluate was concentrated under reduced pressure to obtain 7.9 g of Compound 5.

Appearance: colorless powder
Melting Point: 139.0°–141.0° C.
Specific Rotatory Power: $[\alpha]_D^{23}$=–47.4° (C 1.00, $CH_3OH$)
Ultraviolet Absorption Spectrum ($CH_3OH$ solution): $\lambda 0$ max nm ($\epsilon$) 211.0 (shoulder, 4,900), 222.0 (5,900), 277.0 (1,900)
Infrared Absorption Spectrum (KBr tablet): $\nu$ max $cm^{-1}$ 3481, 3359, 3336, 3197, 1751, 1672, 1649, 1610, 1601, 1525, 1512, 1207, 1190, 1122, 1097
FAB-MS Spectrum (matrix: m-nitrobenzyl alcohol): m/z 281 (M+H)
HR-FAB-MS: $C_{13}H_{17}N_2O_5$ Measured: 281. 1137 Calculated: 281. 1138
$^1$H NMR Spectrum (400 MHz, $CD_3OD$ solution): $\delta$ ppm (integral, multiplicity) 2.01(3H, s), 2.03–2.12(1H, m), 2.24–2.32(1H, m), 2.39(2H, t), 4.55(1H, dd), 6.76(2H, d), 6.91(2H, d)
$^{13}$C NMR Spectrum (100 MHz, CD3OD solution): $\delta$ ppm 22.30, 28.10, 32.47, 53.75, 116.68, 123.19, 144.63, 156.53, 172.54, 173.61, 177.36
Elementary Analysis: $C_{13}H_{16}N_2O_5$ Measured: C 55.53 H 5.71 N 9.88 Calculated: C 55.71 H 5.75 N 10.00

EXAMPLE 6:

O,O-bis(N-acetyl-L-glutaminyl)hydroquinone
(Compound 6)

In 1.5 liter of dried THF were dissolved 16.8 g (59.94 mmol) of N-Z-L-glutamine, 3.3 g (29.97 mmol) of hydroquinone and 0.45 g of 4-dimethylaminopyridine, cooled to 0° C., and 12.6 g (61.07 mmol) of DCC was added thereto and stirred at 0° C. for 20 hours. DCU precipitated was removed by filtration, and the filtrate was concentrated under reduced pressure. The residue was dissolved in 1.7 liter of acetic acid, 50 ml of acetic anhydride and 6 g of 10% Pd-C catalyst (50% $H_2O$) were added thereto, and aerated with hydrogen gas for 6 hours. The catalyst was removed by filtration, and the filtrate was concentrated under reduced pressure. The residue was triturated three times with 100 ml of THF and then once with 100 ml of methanol to obtain 5.3 g of Compound 6.

Appearance: colorless powder
Melting Point: 196.0°–197.0° C.
Specific Rotatory Power: $[\alpha]_D^{23}$=–45.7° (c 0.53, DMSO)
Ultraviolet Absorption Spectrum ($CH_3OH$ solution): $\lambda 0$ max nm ($\epsilon$) 217.0 (7,500), 262.0 (500), 267 (shoulder, 400)
Infrared Absorption Spectrum (KBr tablet): $\nu$ max $cm^{-1}$ 3423, 3372, 3203, 2951, 1751, 1660, 1540, 1502, 1419, 1313, 1211, 1182, 1159, 1018, 976, 575, 515
FAB-MS Spectrum (matrix: m-nitrobenzyl alcohol): m/z 451 (M+H)
HR-FAB-MS: $C_{20}H_{28}N_4O_8$ Measured: 451. 1840 Calculated: 451. 1829
$^1$H NMR Spectrum (400 MHz, DMSO-$d_6$ solution): $\delta$ ppm (integral, multiplicity) 1.90(6H, s), 1.90–1.99(2H, m), 2.05–2.14(2H, m), 2.25(4H, t), 4.38(2H, m), 6.81 (2H, brs), 7.16(4H, s), 7.34 (2H, brs), 8.46 (2H, d)
$^{13}$C NMR Spectrum (100 MHz, DMSO-$d_6$ solution): $\delta$ ppm 22.16, 26.27, 31.00, 52.10, 122.64, 147.87, 169.89, 171.03, 173.27
Elementary Analysis: $C_{20}H_{26}N_4O_8$ Measured: C 52.97 H 5.87 N 12.03 Calculated: C 53.33 H 5.82 N 12.44

EXAMPLE 7:

Lotion

TABLE 7

| Ingredient | Amount (%) |
| --- | --- |
| a. 1,3-Butylene Glycol | 10.0 |
| b. Ethanol | 5.0 |
| c. Methyl Parahydroxybenzoate | 0.1 |
| d. N-acetylglutamine-stearyl (Compound 4) | 0.1 |
| e. Wheat Germ Oil | 0.1 |
| f. Polyoxyethylene-glyceryl Pyroglutamate Isostearate (25 E.O.) | 1.0 |
| g. Fragrance | 0.05 |
| h. Purified water | 83.65 |

To a homogeneous solution of ingredients (a) and (h) shown in Table 7 was added a homogeneous solution of ingredients (b), (c), (d), (e), (f) and (g), and the mixture was stirred to obtain a lotion.

COMPARATIVE EXAMPLE 1

Lotion

A lotion was prepared in the same manner as in Example 7 except that NAG was used in place of ingredient (d) (Compound 4).

EXAMPLE 8:

Milky Lotion

TABLE 8

| Ingredient | Amount (%) |
| --- | --- |
| a. Wheat Germ Oil | 3.0 |
| b. Squalane | 4.0 |
| c. N-acetylglutamine-stearyl (Compound 4) | 0.1 |
| d. Sorbitan Monostearate | 1.5 |
| e. Polyoxyethylene-Sorbitan Monostearate (20 E.O.) | 1.5 |
| f. 1,3-Butylene Glycol | 15 |
| g. Triethanolamine | 0.3 |
| h. Methyl Parahydroxybenzoate | 0.1 |
| i. Carboxyvinyl Polymer | 0.1 |
| j. Fragrance | 0.05 |
| k. Purified Water | 74.35 |

Ingredients (a), (b), (c), (d), (e) and (f) shown in Table 8 were melted under heating. An aqueous solution prepared by dissolving ingredients (g) and (h) in a half amount of ingredient (k) under heating was added thereto, and mixed by stirring. A mixture comprising ingredient (i) and the remaining half amount of ingredient (k) was added thereto along with ingredient (j) and mixed by stirring. Then the mixture was cooled to room temperature to obtain a milky lotion.

COMPARATIVE EXAMPLE 2

Milky lotion

A milky lotion was prepared in the same manner as in Example 8 using the ingredients shown in Table 8 except for ingredient (c) (Compound 4).

EXAMPLE 9:

Cream

TABLE 9

| Ingredient | Amount (%) |
| --- | --- |
| a. Squalane | 5.0 |
| b. Isopropyl Myristate | 3.0 |
| c. Wheat Germ Oil | 3.0 |
| d. Bees Wax | 5.0 |
| e. Cetanol | 2.0 |
| f. Stearic Acid | 4.0 |
| g. Gricerine Monostearate | 3.0 |
| h. N-acetylglutamine-stearyl (Compound 4) | 0.5 |
| i. Triethanolamine | 0.4 |
| j. Methyl Parahydroxybenzoate | 0.1 |
| k. 1,3-Butylene Glycol | 5.0 |
| l. Fragrance | 0.05 |
| m. Purified Water | 68.95 |

Ingredients (a), (b), (c), (d), (e), (f), (g) and (h) shown in Table 9 were melted under heating. An aqueous solution prepared by dissolving ingredients (i), (j), (k), (l) and (m) under heating was added thereto, and mixed by stirring. The mixture was cooled to room temperature to obtain a cream.

EXAMPLE 10

Face Wash

TABLE 10

| Ingredient | Amount (%) |
| --- | --- |
| a. Myristic Acid | 25.0 |
| b. Stearic Acid | 6.0 |
| c. Stearic Acid Diethanolamide | 4.0 |
| d. Ethylene Glycol Monostearate | 1.0 |
| e. N-acetylglutamine-stearyl (Compound 4) | 0.1 |
| f. Methyl Parahydroxybenzoate | 0.1 |
| g. Potassium Hydroxide | 6.0 |
| h. 1,3-Butylene Glycol | 10.0 |
| i. White Sugar | 4.0 |
| j. Fragrance | 0.05 |
| k. Purified Water | 43.75 |

Ingredients (a), (b), (c), (d) and (e) shown in Table were melted under heating. An aqueous solution prepared by dissolving ingredients (f), (g), (h), (i) and (k) under heating was added thereto, and mixed by stirring. Then, ingredient (j) was added thereto and mixed by stirring. The mixture was cooled to room temperature to obtain a face wash.

EXAMPLE 11

Sunscreen Milky Lotion

TABLE 11

| Ingredient | Amount (%) |
| --- | --- |
| a. Propylene Glycol | 4.0 |
| b. N-acetylglutamine-stearyl (Compound 4) | 0.6 |
| c. Titanium Dioxide | 3.0 |
| d. Stearic Acid | 1.0 |
| e. Liquid Paraffin | 1.0 |
| f. Polyoxyethylene-Sorbitan Monostearate (20 E.O.) | 1.5 |
| g. Oleophilic Glycerine Stearate | 1.0 |
| h. Triethanolamine | 0.7 |
| i. Methyl Parahydroxybenzoate | 0.2 |
| j. Carboxyvinyl Polymer | 0.2 |
| k. Fragrance | 0.05 |
| l. Purified Water | 86.75 |

Ingredients (a) and (b) shown in Table 11 were melted under heating, and ingredient (c) was added thereto. The mixture was uniformly dispersed using a three-roll mill to prepare a pigment part. Ingredients (d) and (e) were melted under heating. An aqueous solution prepared by dissolving ingredients (f), (g), (h), (i), (j), (l) and the pigment part under heating was added thereto and mixed by stirring. Ingredient (k) was added thereto and mixed by stirring. The mixture was cooled to room temperature to obtain a sunscreen milky lotion.

EXAMPLE 12

Sunscreen Milky Lotion

A sunscreen milky lotion was prepared in the same manner as in Example 11 except that ingredient (c) * coated with ingredient (b) was used in place of ingredients (b) (Compound 4) and (c) (titanium dioxide).

* In 30 ml of ethyl alcohol was dissolved 0.2 g of Compound 4 under heating, then, 10 g of titanium dioxide were added thereto and uniformly dispersed. After the solvent was removed by distillation, the dried product was powdered to obtain a powder (having a mean particle size of 0.05 microns) of titanium dioxide coated with Compound 4.

EXAMPLE 13

Hair Growth Stimulating Tonic

TABLE 12

| Ingredient | Amount (%) |
| --- | --- |
| a. N-acetylglutamine-isostearyl (Compound 2) | 2 |
| b. Ethanol | 55 |
| c. Propylene Glycol | 5 |
| d. DL-α-tocopherol Acetate | 0.1 |
| e. POE(60)-Hardened Castor Oil | 0.5 |
| f. Fragrance | 0.1 |
| g. Purified Water | 37.3 |

Ingredients (b) and (g) shown in Table 12 were uniformly mixed. A liquid mixture prepared by mixing ingredients (a), (c), (d), (e) and (f) under heating was added thereto and stirred uniformly to obtain a hair growth stimulating tonic.

We claim:

1. An N-acylglutamine derivative of formula (I):

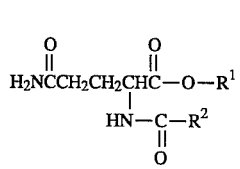

wherein $R^1$ represents

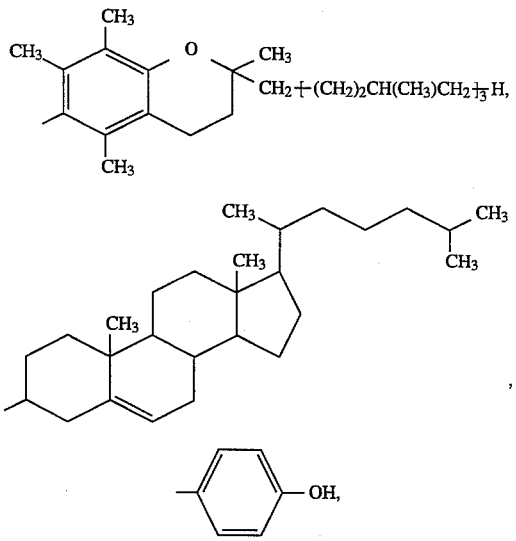

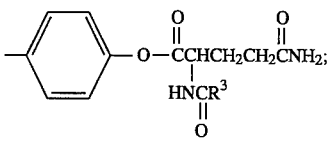

wherein $R^3$ represents an alkyl having 1 to 6 carbon atoms; and $R^2$ represents an alkyl having 1 to 6 carbon atoms.

2. N-acetylglutamine-tocopheryl.

3. N-acetylglutamine-cholesteryl.

4. O-(N-acetyl-L-glutaminyl) hydroquinone.

5. O,O-bis (N-acetyl-L-glutaminyl) hydroquinone.

6. A composition comprising an effective amount of N-acylglutamine derivative of formula (I) as defined in claim 1 and a cosmetic component.

7. A composition according to claim 6, further comprising a pigment.

8. A composition comprising a hair growth stimulant and an effective amount of N-acylglutamine derivative of formula (I) as defined in claim 1.

* * * * *

UNITED STATES PATENT AND TRADEMARK OFFICE
CERTIFICATE OF CORRECTION

PATENT NO. : 5,468,474

DATED : November 21, 1995

INVENTOR(S): Shinkichi Honda et al.

It is certified that error appears in the above-identified patent and that said Letters Patent is hereby corrected as shown below:

COLUMN 3

Line 4, "abovementioned" should read --above-mentioned--.

COLUMN 5

Line 59, "alcohol.Alcohols" should read --alcohol. Alcohols.

COLUMN 6

Line 34, "halocarban." should read --halocarbon.--
Line 41, "maybe" should read --may be--
Line 61, "antiinflammatory" should read --anti-inflammatory--.

COLUMN 7

Line 8, "monooleate," should read --mono-oleate,--
Line 10, "monooleate," should read --mono-oleate,--
Line 12, "hinokitiol," should read --hinokitol,--
Line 13, "triclosan," should read --triclosane,--
Line 55, "Compound." should read --Compound--.

UNITED STATES PATENT AND TRADEMARK OFFICE
CERTIFICATE OF CORRECTION

PATENT NO. : 5,468,474

DATED : November 21, 1995

INVENTOR(S): Shinkichi Honda et al.

It is certified that error appears in the above-identified patent and that said Letters Patent is hereby corrected as shown below:

COLUMN 10

Line 16, "and." should read --and--
Line 30, "(M+I)" should read --(M+1)--.

COLUMN 11

Line 25, "441.3 685" should read --441.3685--
Line 32, "$^3$C" should read --$^{13}$C--.

COLUMN 12

Line 14, "557. 4136" should read --557.4136--
Line 37, "tool)" should read --mol)--
Line 40, "tool)" should read --mol)--
Line 51, "118°119.0°C." should read --118°C-119°C
Line 61, "p0" should be deleted.

COLUMN 13

Line 27, "λ0" should read --λ--
Line 35, "281. 1137" should read --281.1137

UNITED STATES PATENT AND TRADEMARK OFFICE
CERTIFICATE OF CORRECTION

PATENT NO. : 5,468,474

DATED : November 21, 1995

INVENTOR(S) : Shinkichi Honda et al.

It is certified that error appears in the above-identified patent and that said Letters Patent is hereby corrected as shown below:

Line 36, "281. 1138" should read --281.1138--
    Line 41, "CD30D" should read --CD$_3$OD--
    Line 63, "triturated" should read --titrated--.

COLUMN 14

Line 2, "λ0" should read --λ--
    Line 9, "451. 1840" should read --451.1840--
    Line 10, "451. 1829" should read --451.1829--.

COLUMN 15

Table 9, "Gricerine" should read --Glycerin--.

Signed and Sealed this

Seventh Day of May, 1996

BRUCE LEHMAN

Attest:

Attesting Officer

Commissioner of Patents and Trademarks